United States Patent [19]

Samples et al.

[11] Patent Number: 4,654,361

[45] Date of Patent: Mar. 31, 1987

[54] METHOD OF LOWERING INTRAOCULAR PRESSURE USING MELATONIN

[75] Inventors: John R. Samples; Alfred J. Lewy, both of Portland, Oreg.

[73] Assignee: State of Oregon, acting by and through the Oregon State Board of Higher Education, acting for and on behalf of the Oregon Health Sciences University, Portland, Oreg.

[21] Appl. No.: 822,438

[22] Filed: Jan. 27, 1986

[51] Int. Cl.$^4$ .............................................. A61K 31/40
[52] U.S. Cl. ...................................... 514/419; 514/913
[58] Field of Search ................................ 514/419, 913

[56] References Cited

U.S. PATENT DOCUMENTS

| | | | |
|---|---|---|---|
| 3,642,994 | 2/1972 | Anton-Tay | 514/419 |
| 4,388,324 | 6/1983 | Horrobin | 514/474 |
| 4,393,081 | 7/1983 | Schut et al. | 514/419 |
| 4,535,093 | 8/1985 | Horrobin | 514/560 |
| 4,582,848 | 4/1986 | Nadelson | 514/419 |

FOREIGN PATENT DOCUMENTS 78431  5/1983  European Pat. Off. ............ 514/419

OTHER PUBLICATIONS

Chem. Abst. 102:933f (1985)—Chiou et al.
Chem. Abst. 104:29256q (1986)—Chiou et al.
Chem. Abst. 104:82662v (1986)—Rohde et al.

Primary Examiner—Douglas W. Robinson
Attorney, Agent, or Firm—Millen & White

[57] ABSTRACT

A method of lowering the intraocular pressure in a human having abnormally high intraocular pressure, comprising administering systemically thereto an amount of melatonin effective to lower the intraocular pressure.

7 Claims, 2 Drawing Figures

METHOD OF LOWERING INTRAOCULAR PRESSURE USING MELATONIN

This invention was made with Government Support under contract #5 R01 MH40161-02 awarded by the National Institute of Mental Health. The government has certain rights in this invention.

BACKGROUND OF THE INVENTION

This invention relates to the use of melatonin in ophthalmology, and more particularly, relates to the administration of melatonin to humans to lower intraocular pressure in the treatment of glaucoma.

DESCRIPTION OF THE PRIOR ART

The term glaucoma describes a large group of related eye diseases which are characterized by an increase in intraocular pressure, which causes pathological changes in the optical disk and results in a variety of defects in the field of vision. In general, it is an extremely serious condition which can cause not only severe pain in the eyes but also either blindness or a substantial impairment in vision.

Melatonin (5-methoxy-N-acetyltryptamine), is a hormone that is produced by the pineal gland. It has a well characterized circadian rhythm in the body, with serum levels begining to rise shortly after sunset, peaking at around 2 a.m., and then declining to lower levels. Melatonin has been known for some time and has been involved in a wide variety of both medical and other closely related research topics. For example, U.S. Pat. No. 3,642,944 discloses the symptomatic treatment of humans suffering from epilepsy, Parkinson's disease and behavior disorders such as manic depressive phychosis, etc. by the use of oral or parentenal dosages of melatonin in the range of 0.25 to 30 mg/kg of body weight.

J. Pineal Res., Vol. 1, page 3 (1984), discloses that in male golden hamsters a positive relationship exists between melatonin dosages and the fluid content of the intraocular space. Additionally, this reference suggests that increased melatonin dosages may result in an increase in fluid pressure in the intraocular space. This reference teaches away from the usage of melatonin for reducing intraocular pressure since it suggests that the opposite effect would occur.

An ARVO abstract of Rohde et al, Endogenous control of IOP by melatonin, (May 6-10, 1985) discloses that in chickens, increases in melatonin concentration parallel increases in intraocular pressure. The authors state that their findings provide direct supporting evidence for an earlier suggestion that melatonin is an agent for increasing intraocular pressure (Ophthal. Res., 16:302-306, 1984).

Thus, the most relevant prior art suggests that treatment of a human being suffering from glaucoma with melatonin would increase the intraocular pressure of the subject being so treated.

OBJECTS OF THE INVENTION

It is an object of this invention to provide an effective, nontoxic method for the treatment of abnormally high intraocular pressure in human beings, e.g., such as is exhibited by patients with glaucoma.

Surprisingly, these and other objects of the invention are accomplished through the discovery of an effective, nontoxic method for the reduction of abnormally high intraocular pressure in humans.

SUMMARY OF THE INVENTION

In a method aspect, this invention relates to a method of lowering the intraocular pressure in a human being having abnormally high intraocular pressure, comprising adminstering thereto an amount of melatonin effective to lower the intraocular pressure.

BRIEF DESCRIPTION OF THE DRAWINGS

Various other objects, features and attendant advantages of the present invention will become more fully appreciated as the same becomes better understood when considered in conjunction with the accompanying drawings.

DETAILED DISCUSSION

Figure 1:
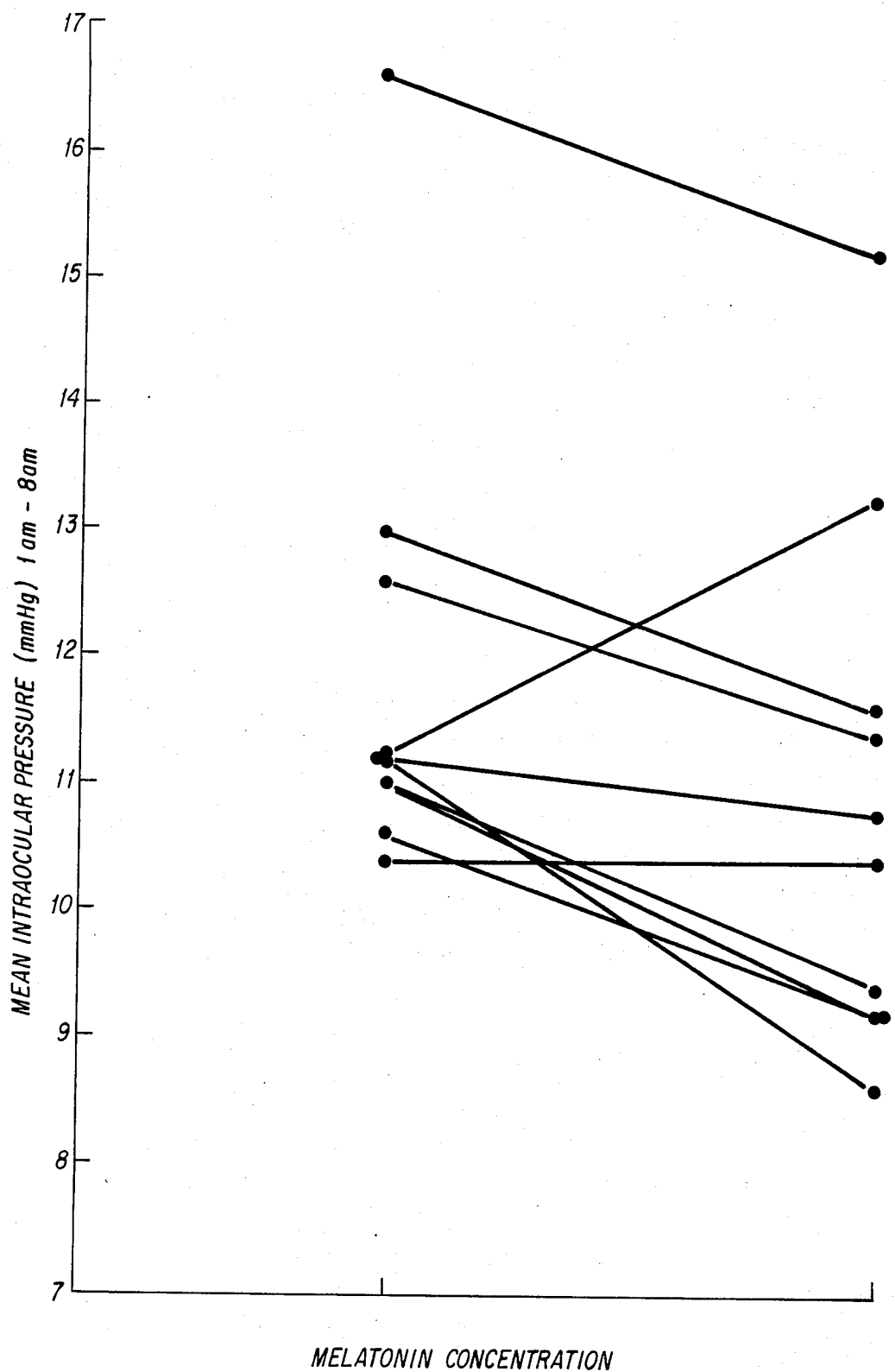
FIG. 1 discloses the changes in intraocular pressure during the period from 1 a.m. to 8 a.m., which is the time in which melatonin normally peaks in the body, for two groups of subjects; one having light suppression in connection with oral melatonin dosages and the second with light suppression alone.

Preferably, the melatonin is administrated in a circadian manner and more preferably coinciding with the natural rise and fall of intraocular pressure in the eyes of humans. Melatonin can be adminstered in a wide variety of methods known to those in the art, e.g. orally, intravenously, topically and the like. The melatonin is administered to the human patient in theraputically effective amounts, e.g., from about 0.30 to 170.0 mg/kg/day, preferably about 3.3 to 16.7 mg/kg/day. The usual total daily oral dose, assuming a 60 kg male, is about 20 micrograms to 20 milligrams per day, preferably about 200 micrograms to 2.0 milligrams per day (assuming the patient is not on any other medication). If the patient is receiving other medication, the administration of melatonin would proceed under conventional state of the art principles of treatment.

Intraocular pressure (IOP) varies diurnally with a mean amplitude of 3 to 7 mm Hg in normal human beings. However, in patients having glaucoma, it is typically greater than 10 mm Hg, with the IOP usually peaking in the early morning hours. This is not always the case however, as many individuals have exhibited other patterns, e.g., some individuals peak in the afternoon, while others have short term fluctuations throughout the day. The art has examined several potential modulators of this circadian change in IOP including epinephrine, serium osmolarity, and cortisol.

Surprisingly, we have discovered that melatonin can be easily and effectively administered so as to decrease the intraocular pressure in humans. This is particularly advantageous since the administration of melatonin appears to be substantially devoid of undesired side effects, with the substance being well absorbed, well tolerated and substantially non-irritating to the tissues and gastrointestinal track of the body. The process of this invention then, in the broadest embodiment, comprises adminstering a therapeutically i.e., pharmacologically, effective amount of melatonin to humans, thereby reducing the intraocular pressure of the administered patient.

The invention, in the broadest embodiment, further comprises a pharmaceutical composition of matter consisting essentially of an intraocular pressure reducing effective amount of the compound melatonin in combination with a non-toxic, pharmaceutically acceptable inert carrier. Such carrier materials are well known to those skilled in the art.

The compounds of the present invention are conveniently administered to humans by either the conventional oral or topical administration, most conventiently by combining melatonin with any effective, non-toxic pharmaceutically-acceptable oral or topical inert carrier material. A member of suitable compounds are disclosed in the reference text entitled "Remington's Pharmaceutical Sciences" (14th Edition), 1970. In a typical form for oral administration, e.g., a tablet or capsule, melatonin is combined with effective oral non-toxic, pharmaceutically acceptable, inert carriers such as lactose, starch (Pharmaceutical Grade), dicalcium phosphate, calcium sulfate, kaolin, mannitol, powdered sugar and the like. Additionally, when required, suitable binders, lubricants, disintegrating agents and coloring agents can also be included. Typical binders include starch, gelatin, sugars, such as sucrose, dextrose and lactose, natural and synthetic gums such as acacia, sodium alginate, extract of Irish moss, carboxymethylcellulose, methylcellulose, polyvinylpyrrolidone, polyethyleneglycol, ethylcellulose and the like.

Typical lubricants for use in these dosages forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alaginic acid, guar, gum, citrus pulp, carboxymethylcellulose and sodium lauryl sulfate. If desired, a conventional pharmaceutically acceptable dye can be incorporated into the dosage unit form, e.g., such as any of the standard FD & C dyes.

Naturally, the therapeutical dosage range for the compounds for the instant invention will vary with the size and needs of the patient. However, generally speaking, the following dosage guidelines will suffice. On an oral basis, the therapeutic dose required for a compound of the instant invention will, generally, range from about 0.30 to 170.0 mg, preferably about 3.3 to 16.7 mg, per kilogram of body weight per day, preferably in divided dosages, e.g., about 4 to 6. The optimum dosage can vary widely from patient to patient. It is preferred to administer melatonin orally, but in emergency situations when a quick response is needed, intravenous administration can be used, as well as a variety of other methods known to those in the art.

The method of administration should take into account the circadian nature of the presence of melatonin in the patient's body, as well as the circadian route of rising and falling IOP. Such methods of regulating the size and time of administration of the melatonin to correspond with the rising and falling intraocular pressure in the patient's body are well known to those in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

Nine normal humans, ranging from 22 to 54 years of age and having normal screening eye examinations, were studied using a randomized crossover design. They were exposed to two different lighting patterns; on the first night they were exposed to bright lights (2500 lux) from 6 p.m. to 6 a.m. to supress the night time rise in melatonin levels. On a subsequent evening they were exposed to dim light (250 lux) during the same time period, thereby coinciding with the normal night time rise in melatonin production by the body. In both experiments intraocular pressure measurements were obtained every two hours starting from 6 p.m. (1800 hr) until 4 p.m. of the following day (1600 hrs) using applanation tonometry with both a Perkins applanation tonometer and a Haig Streit slit lamp tonometer. In both experiments broad spectrum fluorescent lighting was used, with the subjects being kept awake throughout the study. Urine was collected in three periods; 6 p.m. to 1 a.m., 1 a.m. to 8 a.m., and 8 a.m. to 4 p.m.. Urinary 6-hydroxymelatonin was assayed with the use of a gas chromatographic-negative ionization mass spectrometric technique, as described by Lewy and Marky; Science, 201: pg 741–743, (1978). The results of this test set forth the early morning decrease in IOP experienced by the subjects during dim light exposure. This decrease was attentuated during bright light exposure between 2 a.m. and 6 a.m., and particularly at 4 a.m. The IOP was lower during dim light, as compared to bright light exposure. The urinary melatonin levels show that production of melatonin in the body was suppressed by exposure to bright light. 6-Hydroxy-melatonin concentrations measured less than 470 nanograms in the subjects during the periods of bright light exposure and during day time periods. The data disclosed a mean of 5650 nanograms ($\pm 1360$ nanograms) during dim light.

EXAMPLE 2

In this example, the procedures used were the same as those of example 1, except that a third and fourth condition were also included, i.e., the subjects were given either melatonin or an oral placebo when exposed to the bright light. The experiment used 10 subjects which were randomized in a double-blind, crossover study. As in the first example, on alternative nights the subjects were exposed to dim light from 6 p.m. to 6 a.m., or to bright light. Either a placebo or 200 $\mu$g melatonin (obtained from Regis Chemicals, Morton Grove, Ill.) were administered orally in capsules at 10 p.m., 12 p.m., 2 a.m. and 4 a.m. Tonometry was performed every one to two hours from 6 p.m. to 4 p.m. the following day. The results are outlined in FIG. 1, where the circadian rhythm of IOP was similar to that experienced in the first example. As can be seen in FIG. 1, following melatonin administration at 10 p.m. the IOP decreased and remained relatively low, as compared to intraocular pressure measured either during dim light or bright light alone. This effect was particularly pronounced at 11 p.m., 12 p.m. and 6 a.m.. The IOP was not significantly different with bright light as contrasted to dim light exposure. However, the urine 6-hydroxy melatonin levels indicate that melatonin was only partially suppressed with bright light exposure in four of the ten subjects. The melatonin which was orally (200 micrograms, four times) administered was associated with melatonin urine exretion approximately ten times greater than that occurring during the same period of dim light exposure, viz., from 1 to 8 a.m.. The subjects noted no sedation during the night melatonin was administered, although several subjects did complain of eye irritation following the second experiment. The nine subjects whose IOP was lower or unchanged during the melatonin treatment had mean decreases in overall IOP of 1.31 in the dim light period as contrasted the exposure to with bright lights only from 1 a.m. to 8 a.m.. One subject had a IOP which increased.

EXAMPLE 3

Figure 2:
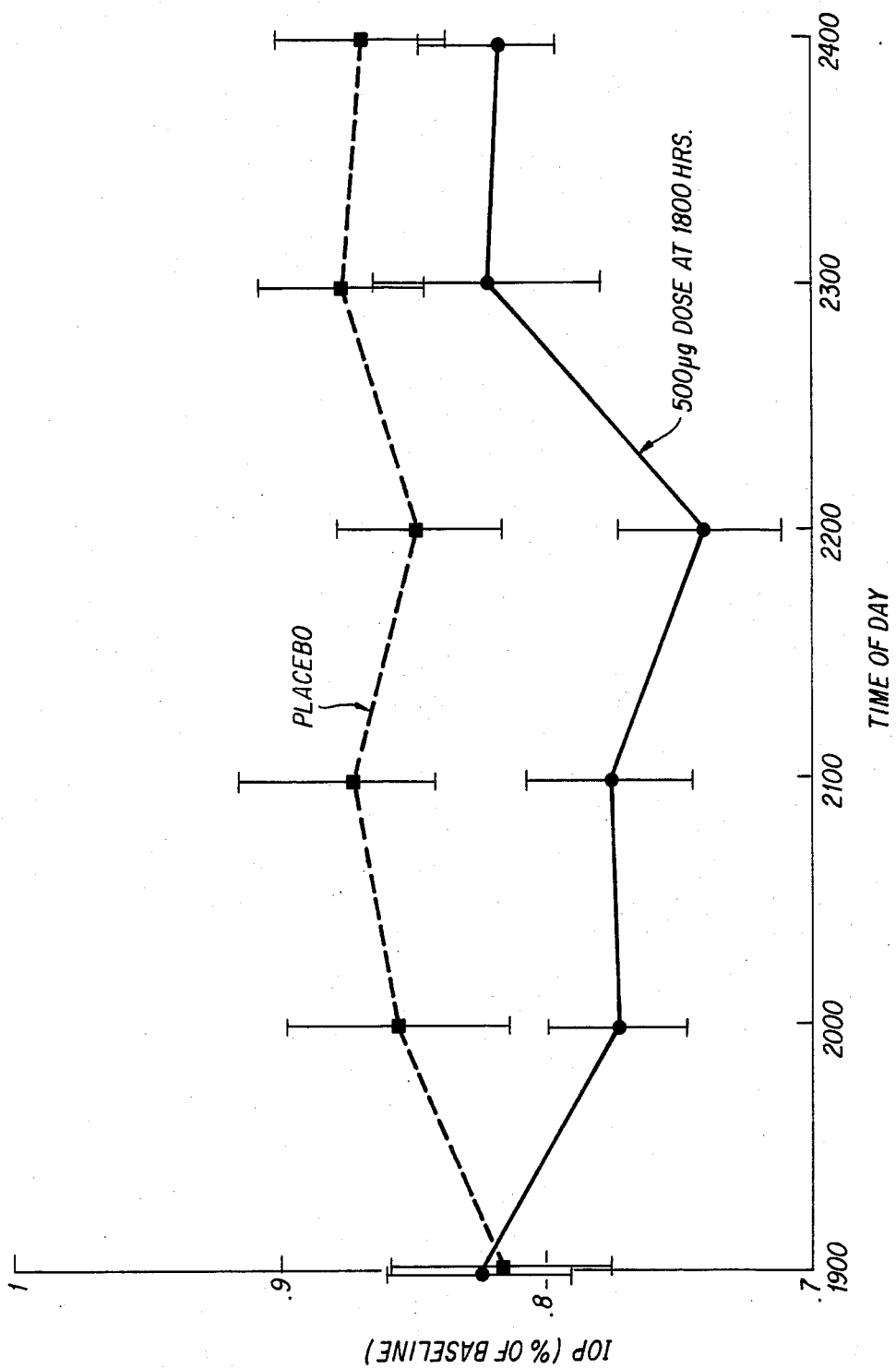
FIG. 2 discloses a second graph displaying the effects of melatonin on IOP for a single dosage given at 6 p.m., one dosage being a placebo and the other containing 500 micrograms of melatonin. The effects are measured from 7:00 until midnight of the same day, with the vertical axis representing IOP as a percentage of the subjects IOP that was measured at 1800 hours.

In this example the subjects were given either a placebo or 500 μg of melatonin at 6 p.m.. Intraocular pressures were monitored on a hourly basis from 5 p.m. to midnight using a randonmized, crossover design. The results are plotted in FIG. 2 for both treated and untreated groups of subjects. In this example, despite an initially slightly higher IOP in the treated group, a significant lowering of IOP occurred in the treated group, as contrasted with those given a placebo. The subjects receiving melatonin had significantly lower intraocular pressure, particularly at 9 and 10 p.m. (p 0.05).

EXAMPLE 4

A middle aged female patient, weighing about 48 kgs, regularly taking no other medication and suffering from open-angle glaucoma, with circadian IOP levels ranging from a daily low of about 22mm Hg to a high of about 36 mm Hg takes orally, on a regular basis, daily dosages of 2.0 mg of melatonin, administered at 4 times a day, approximately every 6 hours; each dosage being 1 tablet containing 0.5 mg of melatonin admixed with bees wax as a diluent and tableting aid. Within about 2-3 days, the daily high IOP is lowered to about 22mm Hg during the period of melatonin therapy.

Our results show that during the period of melatonin's highest levels in the body, the IOP is lowest, with a significant diurnal rhythm in IOP being present. In Example 1, all the subjects had maximum IOP's from 4 p.m. to 6 p.m. and 16 of the 18 subjects had minimums from 2 a.m. to 5 a.m.. In example 1, bright light suppression of melatonin secretion attenuated the early morning fall in IOP, while in the second example, there was only a partial suppression of melatonin production with exposure to bright light, consequently there was not a significant difference in IOP between the subjects exposed to dim light and bright light. However, administering 200 μg of melatonin orally caused a significant decrease in IOP, with the IOP remaining below normal for a approximately four hours after the last dosage.

IOP increased in only in one subject who was the only smoker and who smoked throught the experiment. Nicotine is known to elevate intraocular pressure.

The third example clearly demonstrates a finding of diminished IOP's in humans by a single dosage of melatonin; the effect lasting in this experiment for about four hours.

The diurnal rhythm that we have observed is such that the lowest IOP's are coincident with the night time normal increase in melatonin found in the body. The early morning rise in cortisol also coincides with the rise in IOP. Thus, the discovery that melatonin reduces IOP does not exclude the possibility that cortisol might also be involved.

Although the experiments dealt exclusively with melatonin, it is within the scope of this invention that a wide variety of contemplated equivalents, such as those analogs having inert and non-interferring substituents, groups, and the like might also be within the scope of this invention.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of lowering the intraocular pressure in a human having abnormally high intraocular pressure, comprising
    administering thereto an amount of melatonin effective to lower the intraocular pressure.
2. A method as claimed in claim 1 wherein the human has glaucoma.
3. A method as claimed in claim 1 wherein melatonin is administered in a circadian manner.
4. A method as claimed in claim 1 wherein the melatonin is administered orally.
5. A method as claimed in claim 1 wherein the melatonin is administered topically.
6. A method as claimed in claim 1 wherein the amount of the melatonin administered is from about 0.30 to 170.0 mg/kg/day.
7. A method of lowering the intraocular pressure in a human having abnormally high intraocular pressure, comprising administering melatonin orally on successive days, in an amount from about 3.3 to 16.7 mg/kg/day, to a human being having glaucoma.

* * * * *